United States Patent
Das et al.

(10) Patent No.: US 11,607,308 B2
(45) Date of Patent: Mar. 21, 2023

(54) MULTI-CURVATURE EDGE FOR OPHTHALMIC LENSES

(71) Applicant: ALCON INC., Fribourg (CH)

(72) Inventors: Kamal K. Das, Arlington, TX (US); Jian Liu, Keller, TX (US)

(73) Assignee: Alcon Inc., Fribourg (CH)

( * ) Notice: Subject to any disclaimer, the term of this patent is extended or adjusted under 35 U.S.C. 154(b) by 69 days.

(21) Appl. No.: 16/376,064

(22) Filed: Apr. 5, 2019

(65) Prior Publication Data

US 2020/0197164 A1 Jun. 25, 2020

Related U.S. Application Data (60) Provisional application No. 62/783,617, filed on Dec. 21, 2018.

(51) Int. Cl.
*A61F 2/16* (2006.01)

(52) U.S. Cl.
CPC .......... *A61F 2/1637* (2013.01); *A61F 2/1654* (2013.01); *A61F 2002/1681* (2013.01); *A61F 2002/1696* (2015.04); *A61F 2250/0036* (2013.01)

(58) Field of Classification Search
CPC .................. A61F 2/1637; A61F 2/1654; A61F 2002/1696; A61F 2002/1681; A61F 2250/0036
See application file for complete search history.

(56) References Cited

U.S. PATENT DOCUMENTS

| | | | |
|---|---|---|---|
| 5,755,786 A * | 5/1998 | Woffinden | A61F 2/16 351/159.08 |
| 6,468,306 B1 * | 10/2002 | Paul | A61F 2/16 623/6.16 |
| 9,931,201 B2 | 4/2018 | Angelopoulos et al. | |
| 2001/0018612 A1 * | 8/2001 | Carson | A61F 2/145 623/5.11 |
| 2003/0144733 A1 * | 7/2003 | Brady | G02B 27/0018 623/6.16 |
| 2003/0199976 A1 | 10/2003 | Portney | |
| 2004/0059414 A1 * | 3/2004 | Green | A61F 2/1613 623/6.16 |
| 2005/0246016 A1 * | 11/2005 | Miller | B29D 11/023 351/159.01 |

(Continued)

FOREIGN PATENT DOCUMENTS

| | | |
|---|---|---|
| EP | 1752816 A1 | 2/2007 |
| WO | 2012023937 A1 | 2/2012 |

OTHER PUBLICATIONS

Patent Cooperation Treaty, International Search Report and Written Opinion, Intertational Application No. PCT/IB2019/052823, dated Sep. 2, 2018, 13 pages.

*Primary Examiner* — Javier G Blanco (57) ABSTRACT

An exemplary ophthalmic lens includes an optic comprising an anterior optic surface and a posterior optic, and a multi-curvature optical edge surrounding the optic and connecting the anterior optic surface to the posterior optic surface, the multi-curvature optical edge comprising a plurality of tangentially-connected curved surfaces configured to mitigate positive dysphotopsia by directing or diffusing from light incident on the multi-curvature optical edge away from a fovea of a patient.

10 Claims, 6 Drawing Sheets

(56) References Cited

U.S. PATENT DOCUMENTS

| | | | |
|---|---|---|---|
| 2007/0122450 A1* | 5/2007 | Osio Sancho | A61K 38/47 424/428 |
| 2008/0269390 A1 | 10/2008 | Simpson et al. | |
| 2008/0269891 A1 | 10/2008 | Hong et al. | |
| 2010/0070030 A1* | 3/2010 | Amon | A61F 2/1602 623/6.49 |
| 2014/0005780 A1* | 1/2014 | Zhao | A61F 2/16 623/6.17 |
| 2014/0180408 A1* | 6/2014 | Angelopoulos | A61F 2/1613 623/6.17 |
| 2019/0310493 A1* | 10/2019 | Thompson | G02C 7/04 |

* cited by examiner

MULTI-CURVATURE EDGE FOR OPHTHALMIC LENSES

FIELD OF THE DISCLOSURE

The present disclosure relates to ophthalmic lenses such as intraocular lenses and contact lenses.

BACKGROUND

The human eye includes a cornea and a crystalline lens that are intended to focus light that enters the pupil of the eye onto the retina. However, the eye may exhibit various refractive errors which result in light not being properly focused upon the retina, and which may reduce visual acuity. Ocular aberrations can range from the relatively simple spherical and cylindrical errors that cause myopia, hyperopia, or regular astigmatism, to more complex refractive errors that can cause, for example, halos and starbursts in a person's vision.

Many interventions have been developed over the years to correct various ocular aberrations. These include spectacles, contact lenses, corneal refractive surgery, such as laser-assisted in situ keratomileusis (LASIK) or corneal implants, and intraocular lenses (IOLs). The diagnosis and specification of sphero-cylindrical spectacles and contact lenses for treatment of myopia, hyperopia, and astigmatism are also well-established.

It has been observed that edge portions of a contact lens or implanted IOLs may cause complex refractive errors with undesired effects. Photic phenomena, such as glare (also known as positive dysphotopsia), a shadow (also known as negative dysphotasia), and other undesired visual disturbances can be especially problematic.

SUMMARY

Ophthalmic lenses according present disclosure include one or more multi-curvature optical edges (MCOEs) that can reduce or eliminate dysphotopsias and other undesirable photic phenomena. An exemplary IOL or contact lens includes an optic with anterior and posterior optic surfaces surrounded by and connected to a MCOE. The MCOE may include a plurality of distinct curved surfaces which are tangentially connected to one another. Each of the curved surfaces of the MCOE can have a different radius of curvature. In certain embodiments, the anterior optic surface is tangentially connected to the MCOE. The posterior optic surface may also be tangentially connected to a curved surface of the MCOE, or alternatively the posterior optic surface may connect to a surface of the MCOE at an angle to form an edge or corner configured to inhibit posterior capsular opacification (PCO).

An exemplary ophthalmic lens according to the disclosure includes an optic having an anterior optic surface and a posterior optic surface disposed about an optical axis. The optic may be configured to direct light incident on the anterior optic surface a patient's retina. The optic may include any suitable spherical or aspherical monofocal, multifocal, or extended depth of focus design. A MCOE surrounds the optic and connects the anterior optic surface to the posterior optic surface. The MCOE includes a plurality of curved surfaces configured to mitigate or eliminate glare and/or disphotopsias (positive and/or negative). In particular examples, this may be achieved by configuring the curved surfaces of the MCOE to transmit (e.g., redirect and/or diffuse) light incident on the MCOE away from a patient's fovea. The plurality of curved surfaces of the MCOE includes a first curved surface having a first curvature and a second curved surface having a second curvature. The first curved surface is tangentially connected to the anterior optic surface at a first edge of the first curved surface, and is also tangentially connected to the second curved surface at a second edge of the first curved surface.

The ophthalmic lens may include additional features which may be combined with one another in any manner which that is not clearly mutually exclusive. Examples of such features include:

- a portion of the MCOE connects to the posterior optic surface to form a corner configured to inhibit PCO;
- the second curved surface of the MCOE is connected to the posterior optic surface to form a bi-curvature optical edge;
- the plurality of curved surfaces of the MCOE includes a third curved surface having a third curvature different from the first curvature and the second curvature, the third curved surface tangentially connected to the second curved surface;
- the plurality of curved surfaces of the MCOE includes a fourth curved surface having a fourth curvature different from the first curvature, the second curvature, and a third curvature, the fourth curved surface tangentially connected to the third curved surface;
- all adjacent curved surfaces of the plurality of curved surfaces of the MCOE are tangentially connected;
- a subset of adjacent curved surfaces of the plurality of curved surfaces of the MCOE are tangentially connected;
- each of the plurality of curved surfaces of the MCOE comprises a radius of curvature in the ranges of 0.01 mm and 2.0 mm, 0.05 mm and 1.5 mm, 0.10 mm and 1.0 mm, and 0.25 mm and 0.27 mm;
- the plurality of curved surfaces of the MCOE each have a different radius of curvature;
- the plurality of curved surfaces comprises at least two non-adjacent curved surfaces having the same radius of curvature;
- the MCOE has an edge thickness, measured along the optical axis, in the range of 0.15 mm and 0.45 mm;
- the ophthalmic lens comprises an intraocular lens in which a diameter of the anterior optic surface is in the range of 4.5 mm to 7.5 mm, a diameter of the posterior optic surface is in the range of 5.0 mm to 8.0 mm, and the diameter of the posterior optic surface is greater than the diameter of the anterior optic surface; and
- the ophthalmic lens comprises a contact lens in which a diameter of the anterior optic surface is in the range of 13.5 mm to 15 mm and a diameter of the posterior optic surface is in the range of 13.5 mm to 15 mm.

Another exemplary ophthalmic lens according to the disclosure comprises an intraocular lens (IOL) that includes an optic having an anterior optic surface and a posterior optic surface disposed about an optical axis. The optic may include any suitable spherical or aspherical monofocal, multifocal, or extended depth of focus design. The IOL further includes a MCOE surrounding the optic and connecting the anterior optic surface to the posterior optic surface. The MCOE includes a plurality of curved surfaces configured to mitigate or eliminate glare and/or disphotopsias (positive and/or negative). In particular examples, this may be achieved by configuring the curved surfaces of the MCOE to transmit (e.g., redirect and/or diffuse) light incident on the MCOE away from a patient's fovea. Each one of the plurality of curved surfaces of the MCOE is tangentially connected to at least one adjacent curved surface of the MCOE, and at least two of the plurality of curved surfaces of the MCOE have different radii of curvature.

Further, the IOL may include additional features which may be combined with one another in any manner which that is not clearly mutually exclusive. Examples of such features include:

- each of the plurality of curved surfaces is tangentially connected to at least one adjacent curved surface of the plurality of curved surfaces;
- the plurality of curved surfaces of the multi-curvature optical edge includes exactly two, three, four, five, or six curved surfaces.
- the plurality of curved surfaces of the multi-curvature optical edge includes at least three curved surfaces;
- a first curved surface of the plurality of curved surfaces is tangentially connected to the anterior optic surface;
- a second curved surface of the plurality of curved surfaces is non-tangentially connected to the posterior optic surface to form a corner configured to inhibit PCO;
- each of the plurality of curved surfaces of the MCOE comprises a radius of curvature in the range of 0.01 mm and 2.0 mm;
- the MCOE has an edge thickness, measured along the optical axis, in the range of 0.15 mm and 0.45 mm; and
- a diameter of the anterior optic surface is in the range of 4.5 mm to 7.5 mm, a diameter of the posterior optic surface is in the range of 5.0 mm to 8.0 mm, and the diameter of the posterior optic surface is greater than the diameter of the anterior optic surface.

Another exemplary ophthalmic lens according to the disclosure comprises an intraocular lens that includes an optic having an anterior optic surface with an anterior optic diameter of at least 6.5 mm and a posterior optic surface with a posterior optic diameter larger than the anterior optic diameter. The IOL further includes a multi-curvature optical edge surrounding the optic and connecting the anterior optic surface to the posterior optic surface. The multi-curvature optical edge includes a plurality of tangentially-connected curved surfaces configured to mitigate positive dysphotopsia by redirecting or diffusing light incident on the multi-curvature optical edge away from a fovea of a patient.

Further, the IOL may include additional features which may be combined with one another in any manner which that is not clearly mutually exclusive. Examples of such features include:

- a first curved surface of the multi-curvature optical edge is tangentially connected to the anterior optic surface;
- a second curved surface of the multi-curvature optical edge is non-tangentially connected to the posterior optic surface to form a corner configured to inhibit PCO;
- the multi-curvature optical edge comprises at least three tangentially-connected curved surfaces.
- the multi-curvature optical edge comprises exactly three tangentially-connected curved surfaces.
- the multi-curvature optical edge comprises exactly four tangentially-connected curved surfaces.
- each of the plurality of tangentially-connected curved surfaces of the MCOE comprises a radius of curvature in the range of 0.01 mm and 2.0 mm.
- the multi-curvature optical edge has an edge thickness, measured along the optical axis, in the range of 0.15 mm and 0.45 mm; and
- a diameter of the anterior optic surface is at least 7.0 mm.

It is noted that the above-described examples are illustrative in nature and are not intended to be limiting. The invention encompasses additional variations and combinations of the disclosed features. A particular embodiment of the inventive ophthalmic lens may include any combination of the disclosed features that is not clearly mutually exclusive.

Embodiments of the disclosure provide several benefits and advantages not realized by prior solutions. For example, ophthalmic lenses that include a MCOE as described herein may eliminate or mitigate positive dysphotopsia by redirecting or diffusing light incident on the MCOE optical edge away from a fovea of a patient. Additionally, use of an oversized optic (e.g., greater than 6.0 mm for an IOL) can yield further advantages, eliminating or mitigating negative dysphotopsia by reducing the amount of light incident on the MCOE and focusing more light to the patient's retina. These and other benefits will be recognized by one skilled in the art in light of the present disclosure.

BRIEF DESCRIPTION OF THE DRAWINGS

For a more complete understanding of the present disclosure and its features and advantages, reference is now made to the following description, taken in conjunction with the accompanying drawings, which depict various embodiments of the disclosure.

DETAILED DESCRIPTION

In the following description, details are set forth by way of example to facilitate discussion of the disclosed subject matter. It should be apparent to a person of ordinary skill in the field, however, that the disclosed embodiments are exemplary and not exhaustive of all possible embodiments and furthermore than the component features of the disclosed embodiments may be combined with one another unless clearly mutually exclusive, even though every such combination is not expressly described. It is further noted that the figures are not drawn to scale.

When a patient is wearing a contact lens or has an IOL implanted, the lens may cause undesired photic phenomena in the vision of the patient. Sharp, straight, square, or even some curved edges on a lens can reflect and refract light received at the edges into the foveal area of the retina. To prevent or reduce dysphotopsia and other undesired photic phenomena, the inventors have developed lenses with one or more multi-curvature optical edges (MCOEs). The lenses disclosed herein use MCOEs to direct or diffuse light incident on the edge such that positive dysphotopsia and other undesired photic phenomena are reduced or eliminated. An MCOE may have curved surfaces connected tangentially to prevent the undesired refractions and directed light associated with other edge design. With tangential connections, light can be smoothly transferred from one surface of the MCOE to the next, without directing light at unwanted angles.

Additionally, it is known that patients with large pupils may experience greater glare-like dysphotopsia and other visual disturbances. Lenses that include MCOEs and extended optic diameters can further reduce or eliminate the glare-like dysphotopsia (positive and/or negative) and other visual disturbances in some instances. In particular, an extended optic diameter can provide more usable light for the larger pupil, with a sharper focused image, and can also aid the MCOE to prevent the lens from directing unwanted light received at the MCOE into the foveal area of the eye.

Accordingly, lens designs according to the disclosure can include a MCOE to transmit (e.g., redirect or diffuse) light received at the MCOE away from the foveal area of the patient's retina, thereby reducing positive dysphotopsia, as well as extended optic diameters to complement the MCOE and further reduce negative dysphotopsia. Overall lens performance may thus be improved significantly.

It is noted that particular connections between surfaces described herein may or may not be tangential. For purposes of this disclosure and unless clearly indicated otherwise, a surface is "tangentially" connected to another surface when the connection between the two surfaces is smooth. When not specifically indicated that a connection is tangential, the connection should be read as including connection which may include a tangential connection or other connection such as an angular connection forming a corner.

Figure 1A:
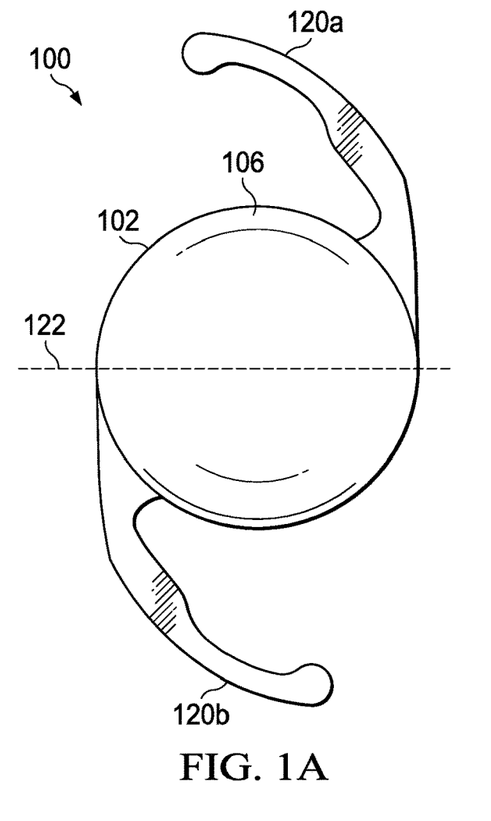
FIGS. 1A and 1B are schematic diagrams of a lens with a multi-curvature optical edge.

FIG. 1A depicts an anterior view of an exemplary intraocular lens (IOL) 100. IOL 100 includes an optic comprising an anterior surface 106 and a posterior surface (not shown) disposed about an optical axis and connected by a multi-curvature optical edge (MCOE) 102. As shown, MCOE 102 surrounds the optic of lens 100 and connects anterior surface 106 to posterior surface 112. IOL 100 may optionally include a plurality of haptics 120a and 120b coupled to the optic to stabilize the optic after implantation. Anterior surface 106 and/or posterior surface 112 may include any suitable spherical, aspheric, refractive, diffractive, or phase shifting features to focus and direct light and improve a patient's vision.

Figure 1B:
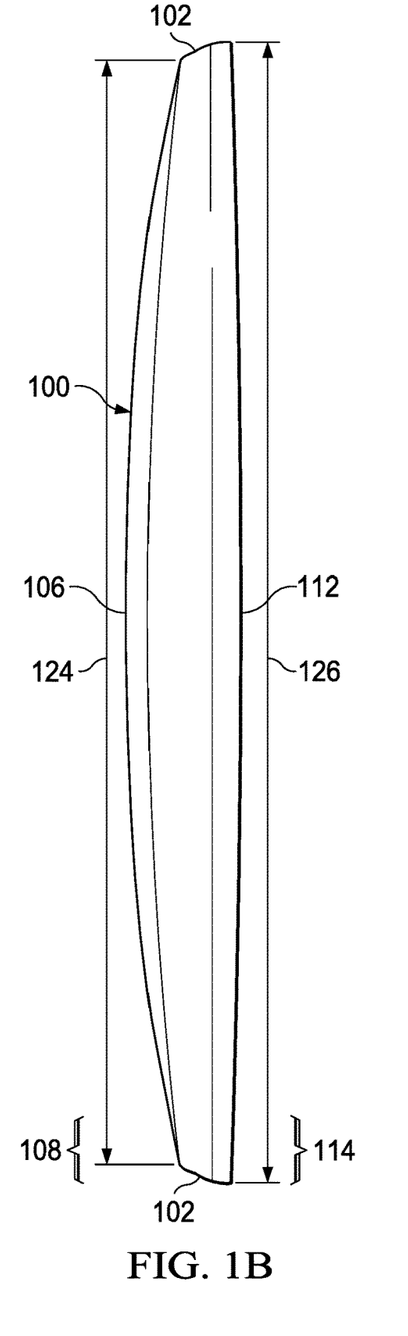

FIG. 1B shows a side or profile of lens 100 viewed along the dotted line 122 of FIG. 1A. Anterior optic surface 106 and posterior optic surface 112 are shown as convex surfaces in FIG. 1B, though other embodiments of anterior optic surface 106 and posterior optic surface 112 may include any suitable combination of concave, convex, or flat surface profiles.

Anterior optic surface 106 of lens 100 is connected to MCOE 102 at anterior optic surface end portion 108, and posterior optic surface 112 is connected to the MCOE 102 at posterior optic surface end portion 114. MCOE 102 includes a plurality of curved external surfaces that are connected tangentially so that light incident on or near MCOE 102 may be refracted, reflected, diffused, and/or otherwise transmitted away from the foveal area of the patient's retina, thereby reducing or eliminating visual disturbances including positive dysphotopsia.

In examples of lens 100 comprising intraocular lenses, the anterior optic surface 106 can have an anterior optical diameter (AOD) 124 in the range of 4.5 mm to 7 mm. The thickness of MCOE in IOL embodiments of lens 100 (measured along the optical axis of lens 100) may be in the range of 0.15 mm and 0.45 mm or higher. In contact lens embodiments of lens 100, the AOD 124 can be in the range of 13.5 mm to 15 mm. As shown in FIG. 1B, AOD 124 is the length of the anterior optic surface 106 between diametrically opposite edges of MCOE 102.

In examples of lens 100 comprising intraocular lenses, the posterior optic surface can have a posterior optical diameter (POD) 126 in the range of 5.0 mm to 8.5 mm. The POD 126 of a given example will depend on AOD 124, and in certain embodiments POD 126 is greater than AOD 124. In contact lens embodiments of lens 100, POD 126 can be in the range of 13.5 mm to 15 mm. As shown in FIG. 1B, POD 126 is the length of the posterior optic surface 112 between diametrically opposite edges of the MCOE 102.

The AOD and POD may be selected based on the size of the eye or pupil of the patient. For example, with IOL embodiments of lens 100, visual disturbances such as positive and negative dysphotopsia can occur more frequently in patients with larger pupil sizes. A relatively larger AOD 124 and POD 126 (e.g., an AOD above 6 mm) can reduce or eliminate glare and other visual disturbances in a lens by allowing the lens optic to receive and focus greater amounts of light to the retina, reducing or eliminating positive dysphotopsia. Moreover, as noted above, directing the light incident on MCOE 201 away from the foveal area of the retina, reducing or eliminating negative dysphotopsia. Accordingly, larger anterior and posterior optic diameters can work in conjunction with a multi-curvature optic edge of embodiments of lens 100 to mitigate or eliminate both positive and negative dysphotopsia.

Figure 2:
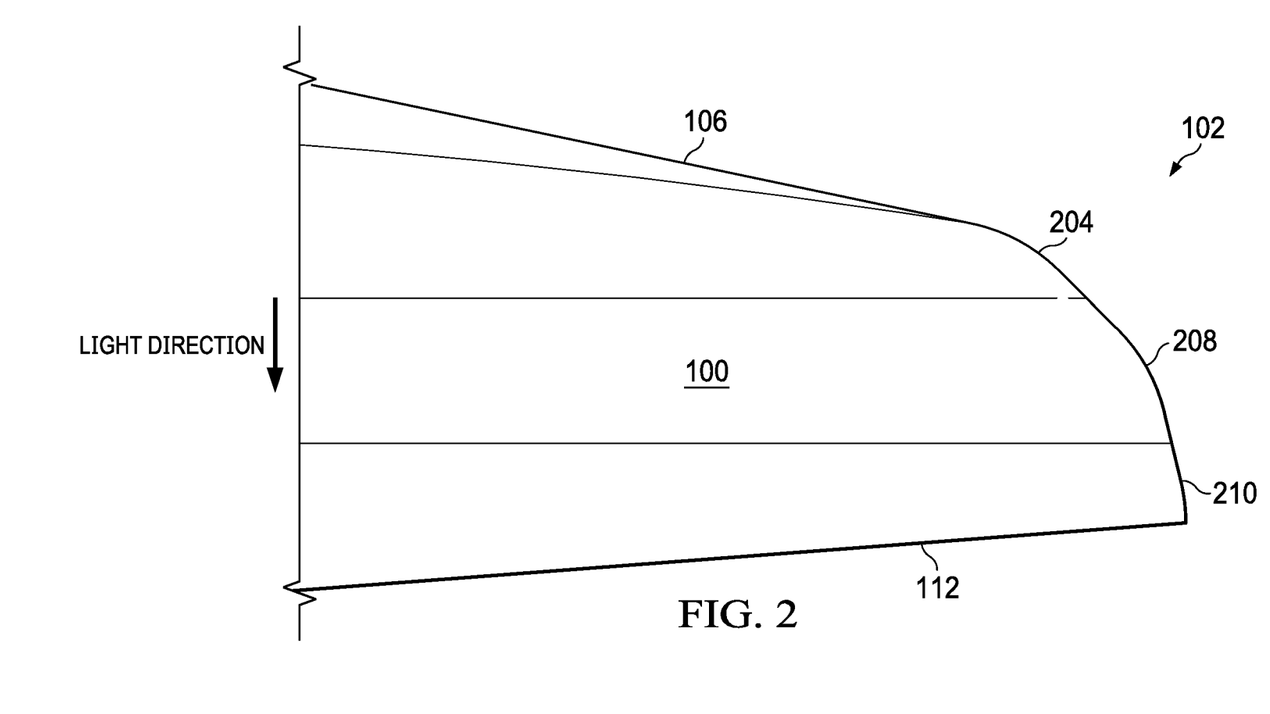
FIG. 2 is a schematic diagram of a multi-curvature optical edge of a lens.

FIG. 2 shows an enlarged view of an example MCOE 102 of a lens 100. MCOE 102 in this example comprises three tangentially-connected curved surfaces. In particular, it includes a first curved surface 204 connected to anterior optic surface 106. In this example, first curved surface 204 is tangentially connected to anterior optic surface 106, but in other embodiments this connection may not be tangential. A second curved surface 208 of the MCOE 200 is tangentially connected to the first curved surface 204. A third curved surface 210 is tangentially connected to the second curved surface 208. The third curved surface 210 is non-tangentially connected to a posterior optic surface 112 to form a corner or edge. In certain embodiments, such a corner or edge may inhibit PCO after implantation of an IOL. In this manner, a lens 100 is provided with a MCOE 200 that has a smooth edge with multiple radii of curvature.

Light incident on the anterior optic surface 206 is focused by the optic surfaces (anterior and posterior) to enhance vision of a patient. Light incident on the MCOE 200, however, is directed away from the fovea to eliminate or mitigate positive dysphotopsia (e.g., glare). More specifically, the path of light incident on MCOE 200 depends in part on the shape of the surfaces it encounters. First curved surface 204, second curved surface 208, and third curved surface 210 each have a different radius of curvatures so that the light can be directed to desired locations, away from the foveal area of the patient's retina. The first curved surface 204 is shown with a first curvature that is not equivalent to a second curvature of the second curved surface 208. The third curved surface 210 has a third curvature that is not equivalent to the curvature of the second curved surface 208 or the first curved surface 204. Each curvature can be varied to adjust where incident light is directed and diffused.

To control how light is directed, various embodiments of lens 100 may include an MCOE 200 having a different number of curved surfaces. That is, although MCOE 200 is shown having three curved surfaces, other embodiments of lens 100 may have an MCOE 200 with two, three, four, five, six, or more curved surfaces. In some embodiments, each curved surface of MCOE 200 is tangentially connected to adjacent curved surfaces. For instance, a lens can have an additional plurality of curved surfaces in addition to the first curved surface 204, the second curved surface 208, and the third curved surface 210. One or more additional curved surfaces could be formed between the third curved surface 210 and the posterior optic surface 212. Such additional curved surface(s) could be tangentially connected to the third curved surface 210 at a first end portion of the additional curved surfaces. As another example, one or more additional curved surfaces could additionally or alternatively be connected to the posterior optic surface 212 at a second end portion of the additional curved surfaces. Alternative embodiments may include a lens having an MCOE comprising any suitable number of curved surfaces tangentially connected between the anterior surface 206 and posterior surface 212.

Different curvatures and different numbers of curved surfaces allow for different directional and diffusive properties of an MCOE to optimize reduction or elimination of dysphotopsia or other undesired photic phenomena based on the shape of the eye, size of the eye, needs of the particular patient, or a combination thereof. Any two or more curvatures of an MCOE may also be equivalent, in particular embodiments.

FIGS. 3 through 6 illustrate examples of how a MCOE may be formed by various curved surfaces for different lenses. In each of the illustrated examples of FIGS. 3 through 6, each curved surface is tangentially connected to another one or two curved surfaces adjacent to it. Although each of the depicted examples depicts an MCOE with three curved surfaces, the MCOE may have two curved surfaces or more than three curved surfaces.

Figure 3:
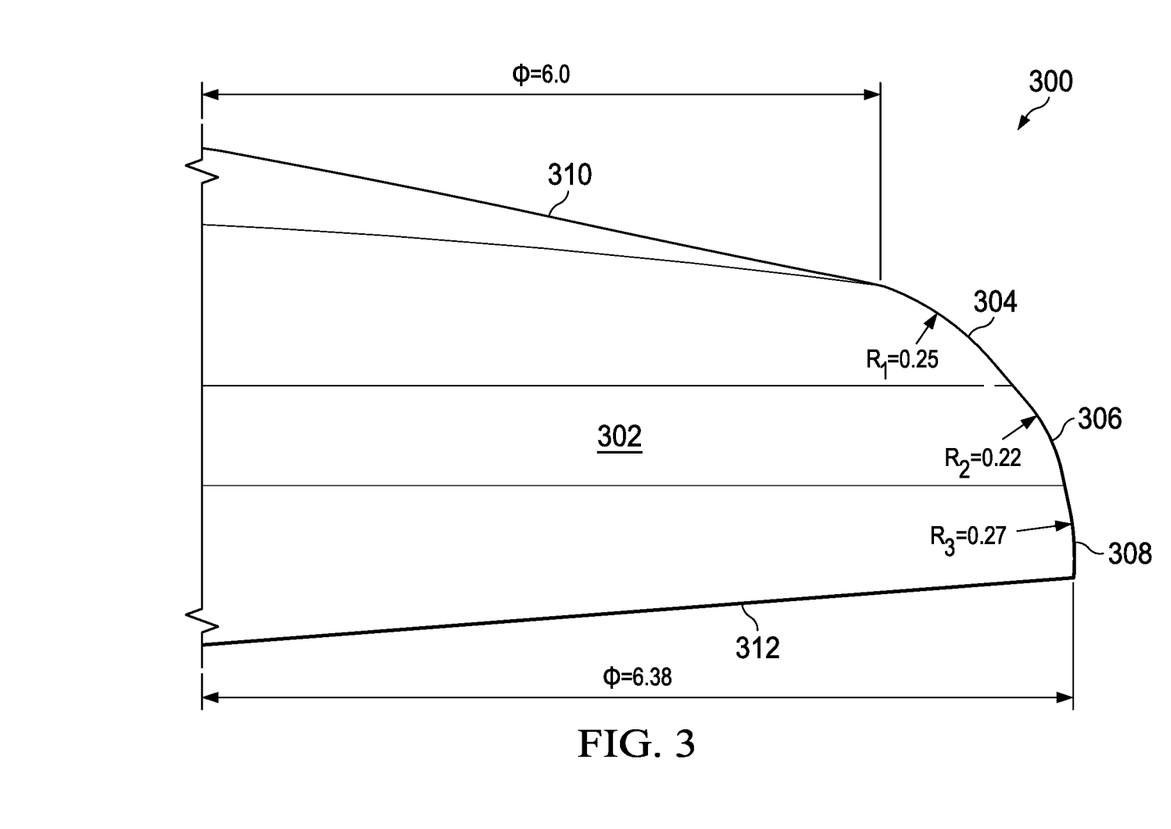
FIG. 3 is a schematic diagram of a multi-curvature optical edge of a lens with a first exemplary set of radii.

FIG. 3 illustrates an example of an MCOE 300 of a lens 302. A portion of the lens 302 is shown. The MCOE has a first curved surface 304, a second curved surface 306, and a third curved surface 308. The first curved surface 304 has a first curvature with a radius of 0.25 mm. The second curved surface 306 has a second curvature with a radius of 0.22 mm. The third curved surface 308 has a third curvature with a radius of 0.27 mm. An anterior surface 310 has an anterior optic diameter (AOD) of 6.0 mm. A posterior optic surface 312 has a posterior optical diameter (POD) of 6.38 mm.

Figure 4:
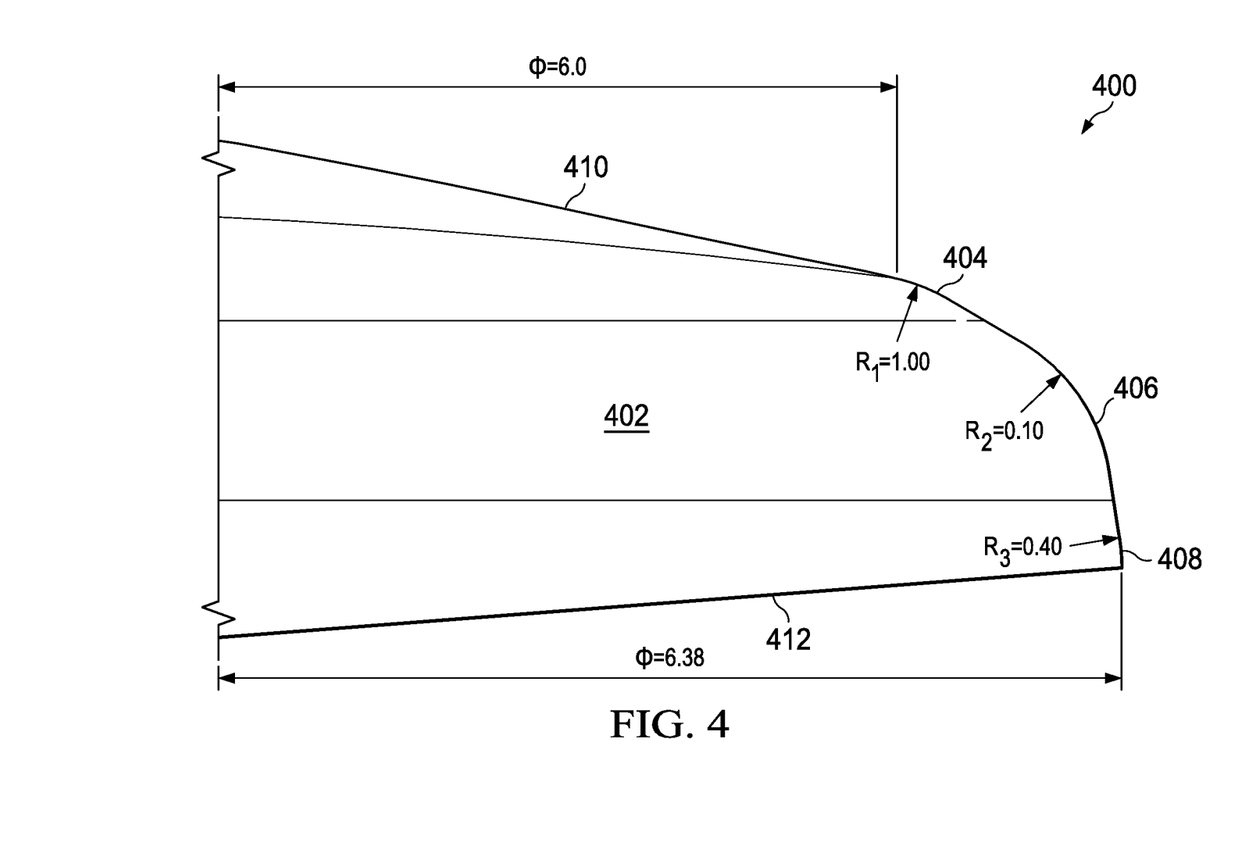
FIG. 4 is a schematic diagram of a multi-curvature optical edge of a lens with a second exemplary set of radii.

FIG. 4 illustrates an example of an MCOE 400 of a lens 402. A portion of the lens 402 is shown. The MCOE has a first curved surface 404, a second curved surface 406, and a third curved surface 408. The first curved surface 404 has a first curvature with a radius of 1.0 mm. The second curved surface 406 has a second curvature with a radius of 0.10 mm. The third curved surface 408 has a third curvature with a radius of 0.40 mm. An anterior surface 410 has an anterior optic diameter (AOD) of 6.0 mm. A posterior optic surface 412 has a posterior optical diameter (POD) of 6.38 mm.

Figure 5:
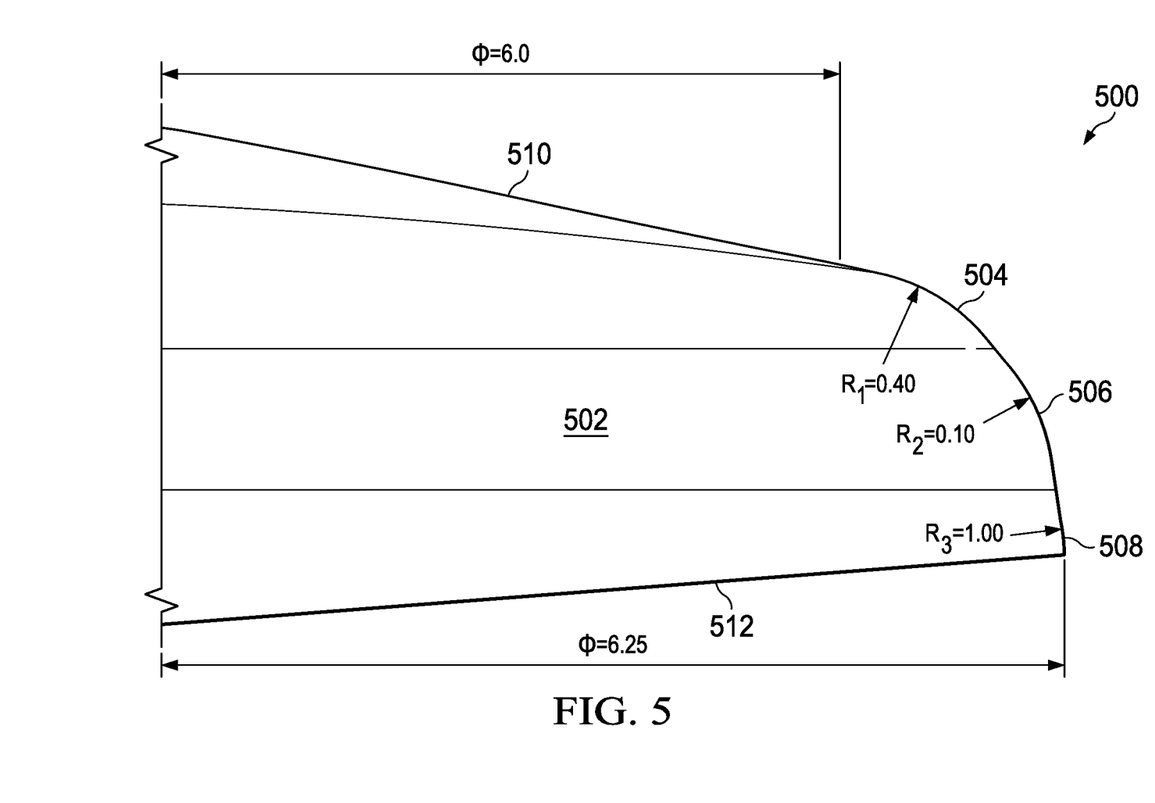
FIG. 5 is a schematic diagram of a multi-curvature optical edge of a lens with a third exemplary set of radii.

FIG. 5 illustrates an example of an MCOE 500 of a lens 502. A portion of the lens 502 is shown. The MCOE has a first curved surface 504, a second curved surface 506, and a third curved surface 508. The first curved surface 504 has a first curvature with a radius of 0.40 mm. The second curved surface 506 has a second curvature with a radius of 0.10 mm. The third curved surface 508 has a third curvature with a radius of 1.0 mm. An anterior surface 510 has an anterior optic diameter (AOD) of 6.0 mm. A posterior optic surface 512 has a posterior optical diameter (POD) of 6.25 mm.

Figure 6:
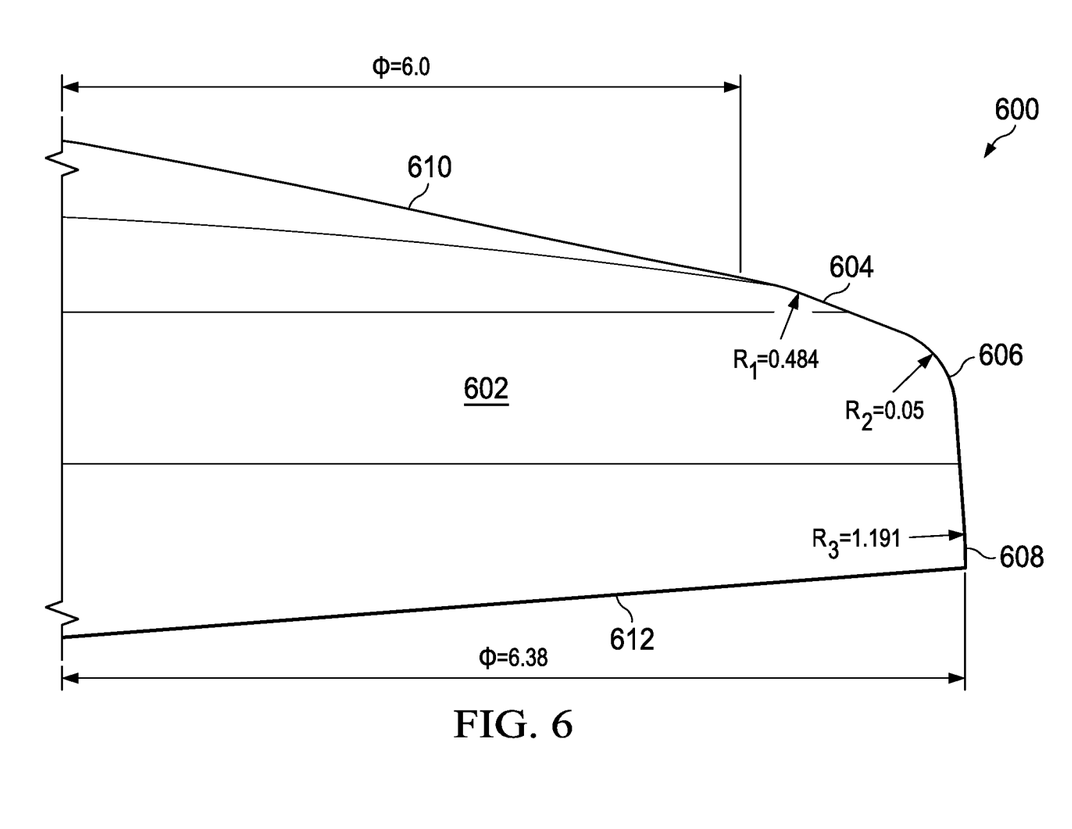
FIG. 6 is a schematic diagram of a multi-curvature optical edge of a lens with a fourth exemplary set of radii.

FIG. 6 illustrates an example of an MCOE 600 of a lens 602. A portion of the lens 602 is shown. The MCOE has a first curved surface 604, a second curved surface 606, and a third curved surface 608. The first curved surface 604 has a first curvature with a radius of 0.848 mm. The second curved surface 606 has a second curvature with a radius of 0.05 mm. The third curved surface 608 has a third curvature with a radius of 1.191 mm. An anterior surface 610 has an anterior optic diameter (AOD) of 6.0 mm. A posterior optic surface 612 has a posterior optical diameter (POD) of 6.38 mm.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents and shall not be restricted or limited by the foregoing detailed description.

The invention claimed is:

1. An intraocular lens comprising:
   an optic having an anterior optic surface and a posterior optic surface disposed about an optical axis, wherein the posterior optic surface comprises a convex curvature, and wherein a diameter of the posterior optic surface is greater than a diameter of the anterior optic surface;
   a multi-curvature optical edge surrounding the optic and connecting the anterior optic surface to the posterior optic surface, the multi-curvature optical edge comprising a plurality of curved surfaces, wherein:
      the plurality of curved surfaces comprises a first curved surface having a first radius of curvature, a second curved surface having a second radius of curvature, and a third curved surface having a third radius of curvature;
      the first curved surface is tangentially connected to the anterior optic surface at a first end of the first curved surface and tangentially connected to the second curved surface at a second end of the first curved surface;
      the second curved surface is tangentially connected to the third curved surface;
      each of the plurality of curved surfaces of the multi-curvature optical edge is convex in shape;
      the first radius of curvature, the second radius of curvature, and the third radius of curvature are different; and
      the multi-curvature optical edge does not include any transitional tangents parallel to the optical axis.

2. The intraocular lens of claim 1, wherein at least one of the curved surfaces of the multi-curvature optical edge is configured to redirect light incident on the multi-curvature optical edge away from a patient's fovea.

3. The intraocular lens of claim 1, wherein at least one of the curved surfaces of the multi-curvature optical edge is configured to diffuse light incident on the multi-curvature optical edge away from a patient's fovea.

4. The intraocular lens of claim 1, wherein the multi-curvature optical edge connects to the posterior optic surface to form a corner edge.

5. The intraocular lens of claim 1, wherein the third curved surface is connected to the posterior optic surface.

6. The intraocular lens of claim 1, wherein the plurality of curved surfaces further comprises a fourth curved surface having a fourth curvature different from the first curvature, the second curvature, and the third curvature, the fourth curved surface tangentially connected to the third curved surface.

7. The intraocular lens of claim 1, wherein each of the plurality of curved surfaces comprises a radius of curvature in the range of 0.01 and 1.50 mm.

8. The intraocular lens of claim 1, wherein:

the diameter of the anterior optic surface is in the range of 4.5 mm to 7.5 mm;
the diameter of the posterior optic surface is in the range of 5.0 mm to 8.0 mm.

9. The intraocular lens of claim 1, wherein the diameter of the anterior optic surface is at least 6.5 mm.

10. The intraocular lens of claim 1, wherein the diameter of the anterior optic surface is at least 7.0 mm.

* * * * *